(12) United States Patent
Tantillo (10) Patent No.: US 7,547,893 B1
(45) Date of Patent: Jun. 16, 2009

(54) INFANT STIMULATION AND ENVIRONMENT STERILIZING DEVICE

(76) Inventor: Sylvia Tantillo, 18509 Barcelona Lake Cir., Delray Beach, FL (US) 33446

( * ) Notice: Subject to any disclaimer, the term of this patent is extended or adjusted under 35 U.S.C. 154(b) by 243 days.

(21) Appl. No.: 11/784,656

(22) Filed: Apr. 9, 2007

Related U.S. Application Data (63) Continuation-in-part of application No. 11/392,014, filed on Mar. 29, 2006, now Pat. No. 7,202,484.

(51) Int. Cl.
| | |
|---|---|
| *A61L 9/00* | (2006.01) |
| *A61L 2/00* | (2006.01) |
| *B08B 3/10* | (2006.01) |

(52) U.S. Cl. .............................. 250/455.11; 250/461.1; 250/504 R; 422/24; 206/575

(58) Field of Classification Search ............ 250/453.11, 250/454.11, 461.1, 504 R, 455.11; 422/22, 422/24, 300; 206/573, 575; 34/26, 209, 34/217; 312/209
See application file for complete search history.

(56) References Cited

U.S. PATENT DOCUMENTS

| | | | |
|---|---|---|---|
| 2,592,131 A | | 4/1952 | Farrar |
| 3,100,842 A | | 8/1963 | Tellefsen |
| 3,711,021 A | | 1/1973 | Tantillo |
| 4,625,119 A | | 11/1986 | Murdock |
| 4,806,770 A | | 2/1989 | Hylton et al. |
| 4,877,964 A | | 10/1989 | Tanaka |
| 4,888,487 A | | 12/1989 | Ritter |
| 4,931,654 A | * | 6/1990 | Horng ........................ 250/436 |
| 5,023,460 A | | 6/1991 | Foster |
| 5,029,252 A | | 7/1991 | Ameseder |
| 5,126,572 A | | 6/1992 | Chu |
| 5,127,521 A | * | 7/1992 | Bourque .................. 206/362.1 |
| 5,160,699 A | | 11/1992 | Siegal |
| 5,166,528 A | | 11/1992 | Le Vay |
| 5,185,532 A | | 2/1993 | Zabsky |
| 5,487,877 A | | 1/1996 | Choi |
| 5,505,904 A | * | 4/1996 | Haidinger et al. ............. 422/24 |
| 5,979,472 A | | 11/1999 | Lowery |
| 6,171,559 B1 | | 1/2001 | Sanders |
| 6,461,568 B1 | | 10/2002 | Eckhardt |
| 6,558,640 B1 | | 5/2003 | Nottingham |
| 6,811,748 B2 | | 11/2004 | Ettlinger |
| 7,202,484 B1 | * | 4/2007 | Tantillo .................. 250/455.11 |
| 2002/0146343 A1 | * | 10/2002 | Jenkins et al. ................. 422/24 |
| 2005/0163652 A1 | * | 7/2005 | Metzger et al. ............... 422/22 |
| 2005/0163653 A1 | * | 7/2005 | Crawford et al. .............. 422/24 |
| 2005/0236579 A1 | * | 10/2005 | Jenkins et al. ......... 250/455.11 |

\* cited by examiner

*Primary Examiner*—Bernard E Souw
(74) *Attorney, Agent, or Firm*—Malin Haley DiMaggio Bowen &Lhota, P.A.

(57) ABSTRACT

A cognitive stimulating sterilizing device for providing visual, tactile and, or audible stimulation for infants while selectively sterilize select items and the surrounding ambient, including a housing adapted for removable connection to cribs, changing tables and similar furniture, ultraviolet light generating source in the housing for sanitizing items in the housing when closed and the ambient when opened, audio source and compartments for holding and storing select items. The housing may include reflective and, or transparent surfaces for directing, reflecting and, or passing ultraviolet light.

17 Claims, 8 Drawing Sheets

INFANT STIMULATION AND ENVIRONMENT STERILIZING DEVICE

CROSS REFERENCE TO RELATED APPLICATIONS

This application is a continuation-in-part of application Ser. No. 11/392,014 filed Mar. 29, 2006.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

This invention relates generally to a crib accessory, and more particularly, to a multi-purpose crib accessory that is mountable to an infant's crib or changing table, selectively emits room sterilizing and sanitizing agents into the environment, includes compartments for holding infant care products and provides visual and audible stimulation to promote cognitive development.

2. Description of the Background Art

It is well known that a clean and mentally stimulating environment is important for facilitating health and cognitive development in an infant. An infant's room is often contaminated with airborne bacteria, unhealthy micro-organisms, germs and other unhealthy conditions in the actual dwelling, such as odors, mold, dirt and, or dust, which can adversely affect an infant's health and cognitive development. Sanitizing agents are typically provided in spray cans or bottles, which require the cognizant caretaker to remember to use them. In fact, they may be harmful if used improperly or excessively or by a child. It is also known that infant brains develop and mature when an infant is exposed to visual, audible and tactile stimulation. Colorful and audible mobiles are known in the art but are limited to providing visual and/or audible stimulation. Infant sanitization and brain stimulating products historically comprise separate articles. However, given the dual needs and concerns, it would be beneficial to provide a safe and effective infant stimulation and environment sterilizing device.

Ultraviolet radiation or UVC is reportedly a reliable and safe sterilizing/sanitizing alternative, but has not been effectively adapted for automatically or controllably sterilizing an infant's immediate environment and items. UV-C, also known as germicidal irradiation, lies in the spectrum between 100 and 280 nanometers (nm)) and is used for purification of air, water and surfaces. Due to its short wavelength, (200 to 270 nm) UV-C penetrates the outer membrane of bacteria, yeasts, molds and viruses, attacking the DNA that makes up their structure. By breaking the chains between the two helixes within the DNA, the microorganism is rendered unable to reproduce, i.e. clinically dead.

Visual and audible mobiles that connect to cribs also exist. However, they fail to offer any environment cleansing benefits or structure for holding infant care products in a conveniently accessible location.

Although various sterilizing products and cognitive development devices are recognized in the prior art, they fail to adequately address or resolve the above noted concerns in a single device for sterilizing the immediate environment while facilitating cognitive growth. The applicant previously obtained U.S. Pat. No. 3,711,021 for a device that suspends from a ceiling and holds hair-grooming articles for use in hair salons, but it fails to address the above noted gap in the prior art. A device that simultaneously and reliably sterilizes an infant's environment while promoting cognitive development, as contemplated by the instant invention, is simply not known. For instance, U.S. Pat. Nos. 2,592,131; 3,100,842; 4,806,770; 4,877,964; 4,888,487; 5,023,460; 5,126,572 and 5,185,532 and U.S. Pat. No. 6,171,559 disclose toothbrush and dental instrument sanitizing devices that merely employ ultraviolet radiation as a sanitation agent. Likewise, U.S. Pat. Nos. 4,625,119; 5,029,252; 5,160,699; 5,166,528; 5,487,877 and 5,979,472 and U.S. Pat. Nos. 6,461,568; 6,558,640 and 6,811,748 only describe devices that utilize ultraviolet light as a sterilizing agent.

As noted, the aforementioned art fails to disclose a device that automatically or controllably employs and emits ultraviolet light to sterilize/sanitize an infant's ambient environment while simultaneously providing visual and audible stimulation for the infant and holding infant care products for conveniently accessible. As the background art fails to disclose a device that adequately addresses these multiple requirements in a single device, there is a need for such a device. The instant invention addresses this need by providing such a device, as contemplated by the instant invention disclosed herein.

BRIEF SUMMARY OF THE INVENTION

Based on the foregoing, it is a primary object of the instant invention to provide a cognitive stimulating sterilizing device for infants.

It is an object of the present invention to provide a cognitive stimulating sterilizing device for infants, toddlers and the like that is mountable or removably moutable to a ceiling or wall.

It is an additional object of the present invention to provide a cognitive stimulating sterilizing device for infants, toddlers and the like that may be electrically connected to a ceiling or wall outlet.

It is another object of the present invention to provide a cognitive stimulating sterilizing device for infants, toddlers and the like that has a rechargeable battery or recharges batteries.

It is a further object of the present invention to provide a cognitive stimulating sterilizing device for infants, toddlers and the like having visible lights and, or patterns using LED's or other light sources.

It is yet another object of the present invention to provide a cognitive stimulating sterilizing device for infants, toddlers and the like having a microcontroller for energizing and de-energizing the ultraviolet light source.

It is also an object of the present invention to provide a cognitive stimulating sterilizing device for infants, toddlers and the like that is mountable to a crib, changing table or other infant support device, using a clamp or other device.

It is another object of the present invention to provide a cognitive stimulating sterilizing device for infants, toddlers and the like that is portable.

It is an additional object of the present invention to provide a cognitive stimulating sterilizing device for infants, toddlers and the like that utilizes ultraviolet light to facilitate sterilization of items placed in the device and the air in the corresponding room.

It is a further object of the present invention to provide a cognitive stimulating sterilizing device for infants, toddlers and the like that provides visual, tactile and, or audible stimulation to facilitate cognitive development.

It is yet another object of the present invention to alternatively provide a cognitive stimulating sterilizing device for infants, toddlers and the like that can hold infant care products in a manner that facilitates convenient access thereto.

It is still another object of the present invention to alternatively provide a cognitive stimulating sterilizing device for infants, toddlers and the like that can warm a baby bottle.

In accordance with these and other objects of the present invention, the instant invention provides a cognitive stimulating sterilizing device for providing visual, tactile and, or audible stimulation for facilitating cognitive development in infants and toddlers while selectively releasing ultraviolet light to sterilize the surrounding ambient by breaking down airborne bacteria, unhealthy microorganisms, odors and germs and that includes storage compartments for holding health care products, such as wipes, powder and lotions and power receiving or generating devices. The cognitive stimulating sterilizing device comprises a housing adapted for removable mounting to a ceiling, wall or floor stand or removable connection to cribs, changing tables and similar furniture or a stand-alone system; ultraviolet light (UV) generating device in the housing for sanitizing objects placed in the housing and the ambient; microcontroller in electrical communication with the UV light source for automatically energizing or de-energizing the UV light source according to one or more preset times; compartments for holding selected items and incandescent light bulb for providing ambient light. The cognitive stimulating sterilizing device temporarily energizes the UV light source for a predetermined period of time, such as 3-6 minutes, when the housing is closed to sterilize items therein and releases the sterilizing ultraviolet light when the housing is opened to sanitize the ambient. The instant invention includes a microprocessor or timer that controls when power is removed from the UV light source. In the preferred embodiment, the instant invention also includes a mobile projecting from the housing to provide visual stimulation. The housing may include reflective and, or transparent surfaces for directing, reflecting and, or passing ultraviolet light. The instant invention may include visible lights, which may form patterns, using LED's or other light sources, preferably controllable by the microcontroller. The instant invention includes a support frame comprising telescopic tubing for adjusting the height of the housing and that is mountable to a crib, changing table or similar furniture by a clamping device. The tubing may include spaced holes that receive a pin for maintaining a selected elevation.

The housing is preferably spherical, comprising two hemispheres releasably engageable together. The housing includes and, or supports visual, audible and, or tactile stimulating devices removably attached to the housing for replacement with other stimulating devices to vary the stimulation. The housing preferably includes a rotatable section, such as a selected hemisphere or auxiliary ring, for providing a rotatable mobile that may be driven by a motor. The housing may also support at least one sound-generating device having one or more sound generating options to provide audible stimulation. The housing may also provide light stimulation and, or tactile stimulation with three-dimensional objects, which may also be caused to move or vibrate. The timer may be connected to the motor for automatically and, or adjustably removing and connecting power to the motor for rotating the mobile and varying speed of rotation.

In accordance with these and other objects, which will become apparent hereinafter, the instant invention will now be described with particular reference to the accompanying drawings.

DETAILED DESCRIPTION OF THE INVENTION

Figure 1:
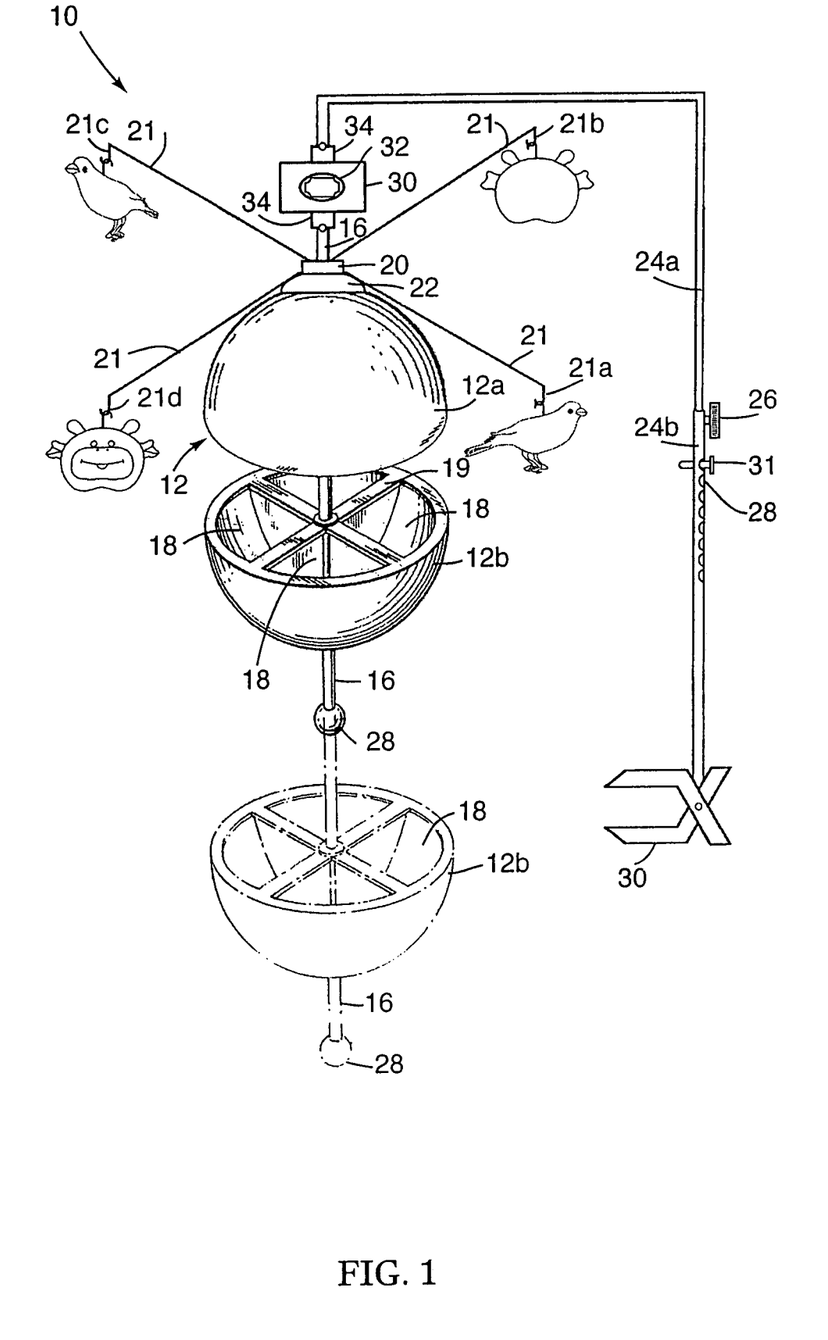
FIG. 1 is a perspective view of the preferred embodiment of the present invention shown in extended and retracted positions.
Figure 2:
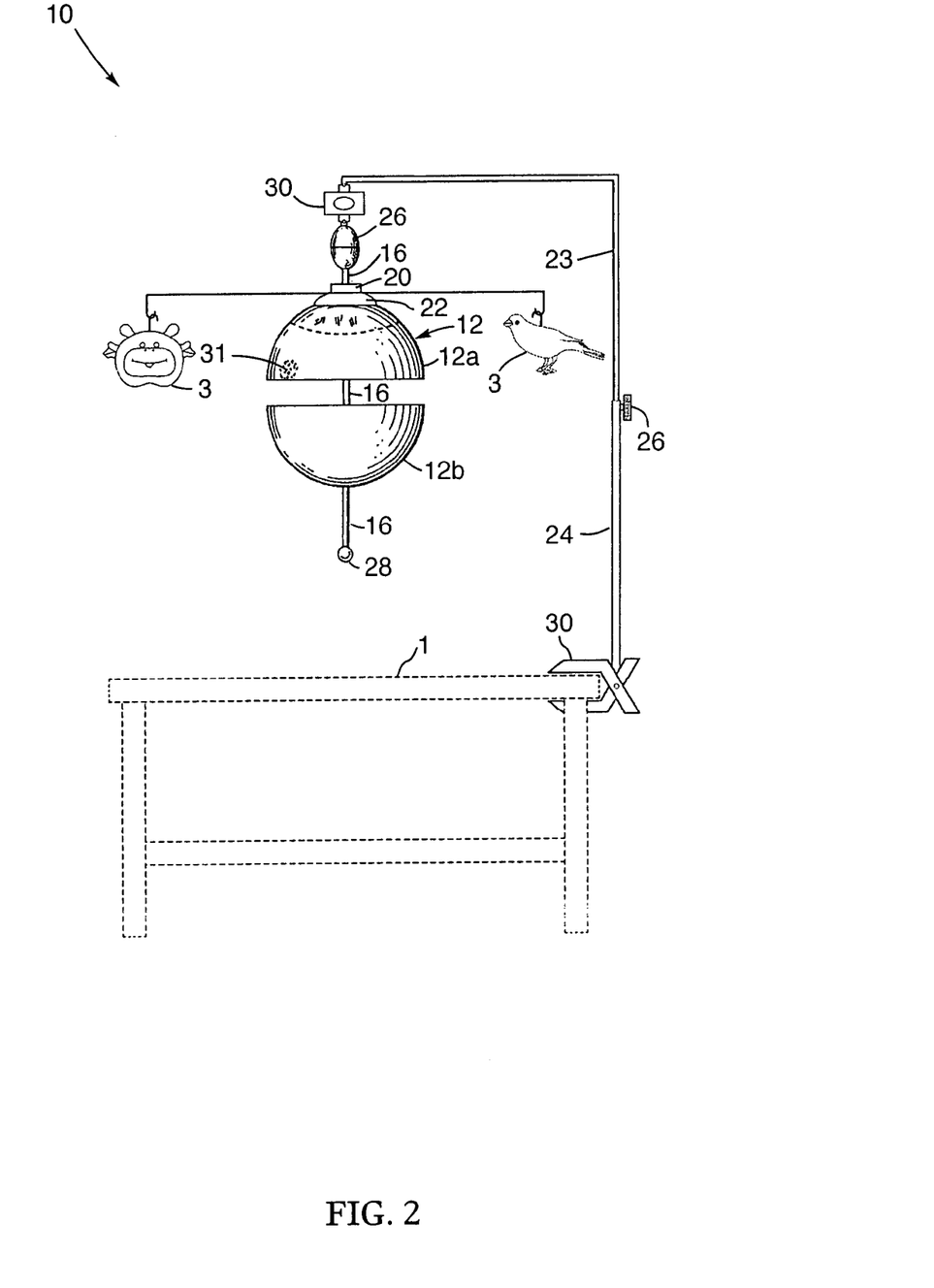
FIG. 2 is an elevational view of another embodiment of the present invention shown in a partially extended position attached to a changing table and having a retraction unit.
Figure 3:
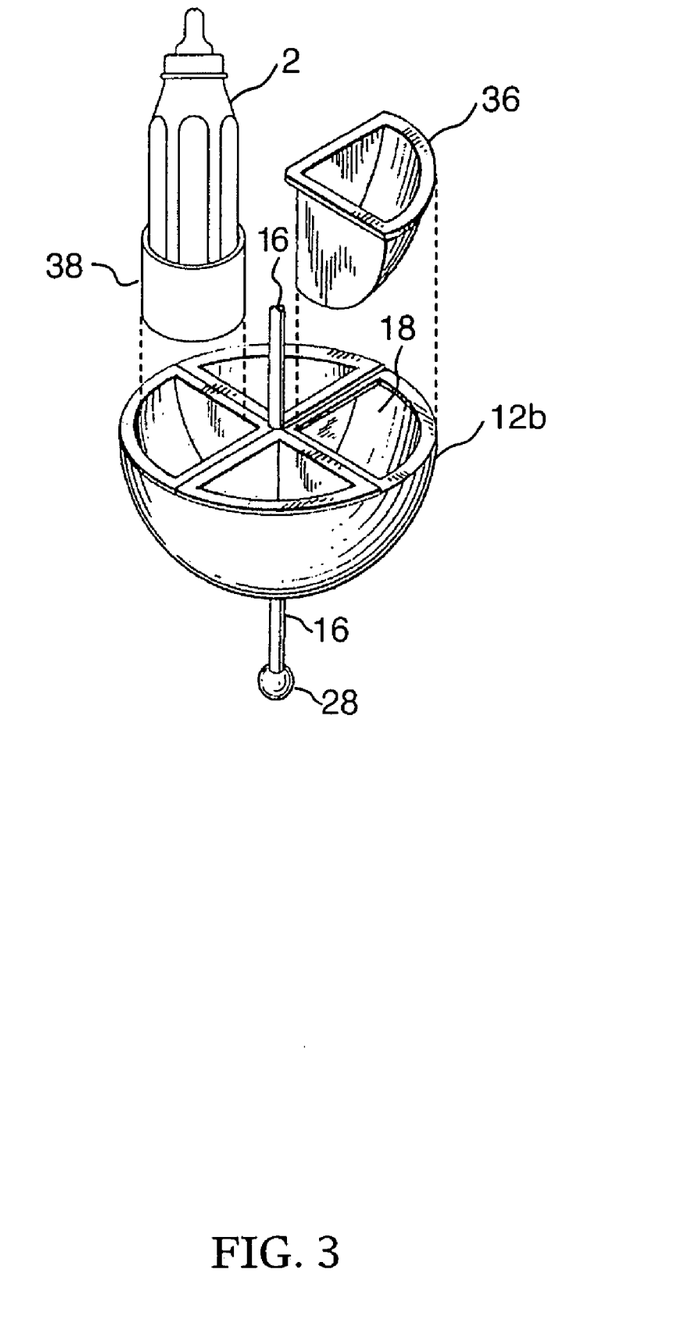
FIG. 3 is a partially exploded view of one embodiment of the instant invention illustrating removable trays and accessories such as bottle warmers.
Figure 4:
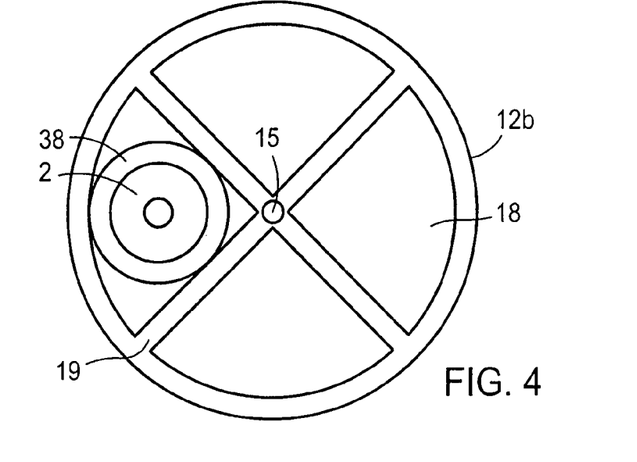
FIG. 4 is a plan view of the lower housing sphere of the instant invention showing the compartments and a bottle in a warmer.
Figure 5:
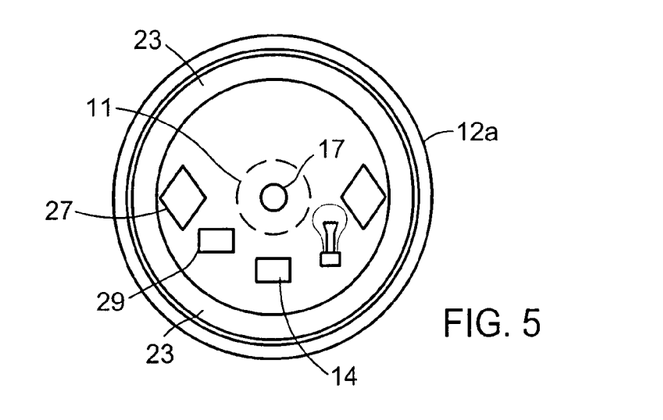
FIG. 5 is a plan view of the upper housing sphere of the instant invention showing the ultraviolet light source.
Figure 6:
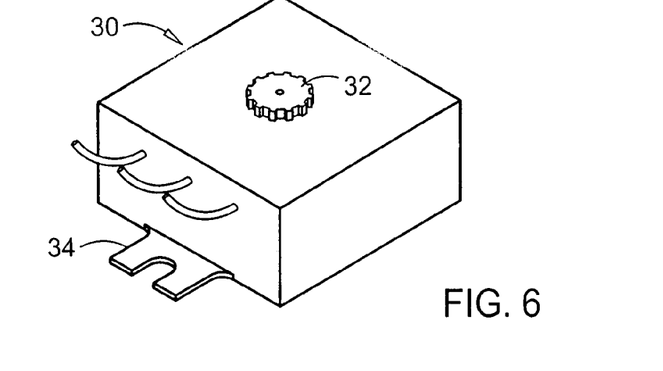
FIG. 6 is a perspective view of the timer of the instant invention.
Figure 7:
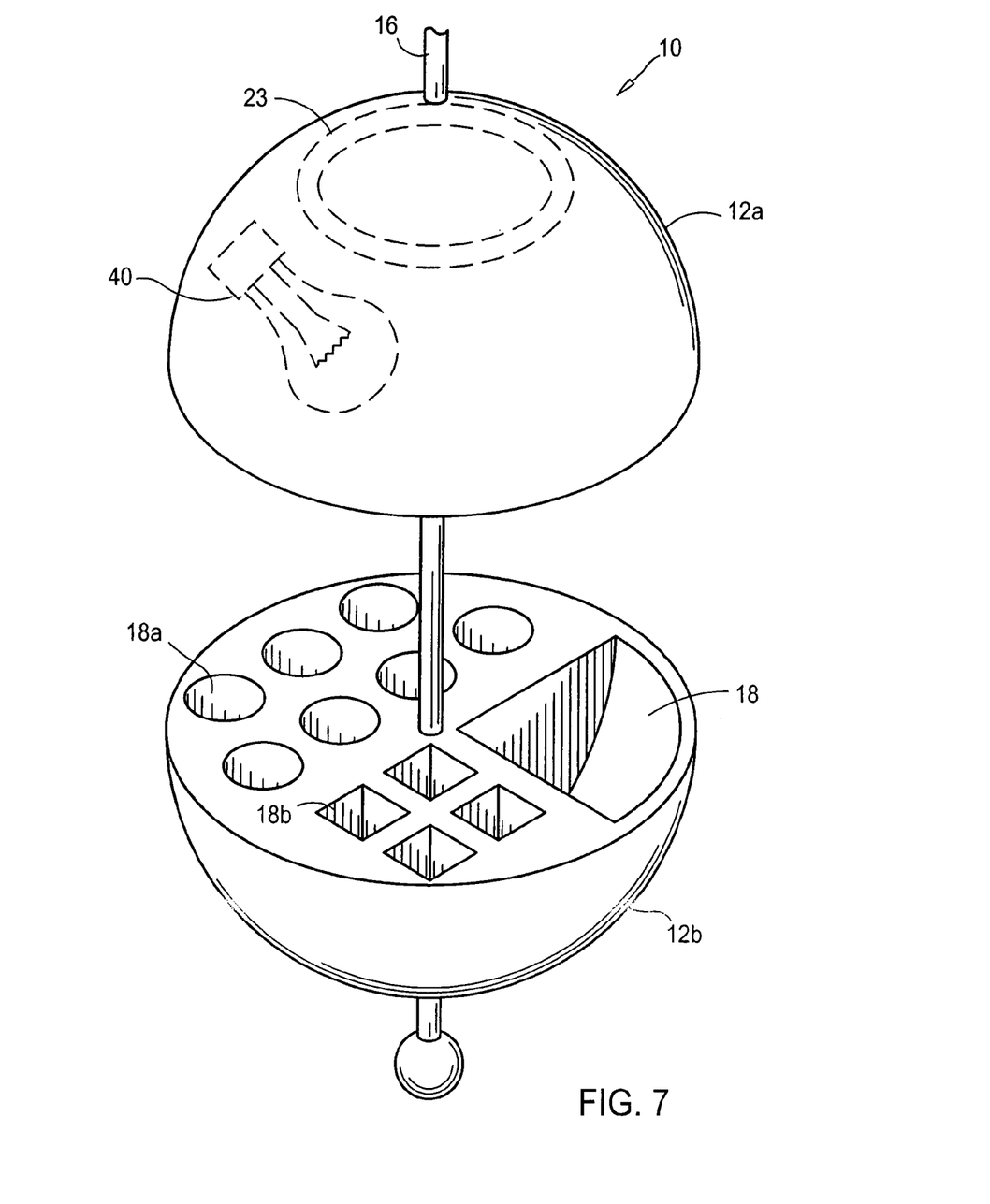
FIG. 7 is a perspective view of an alternative embodiment of the instant invention.
Figure 8:
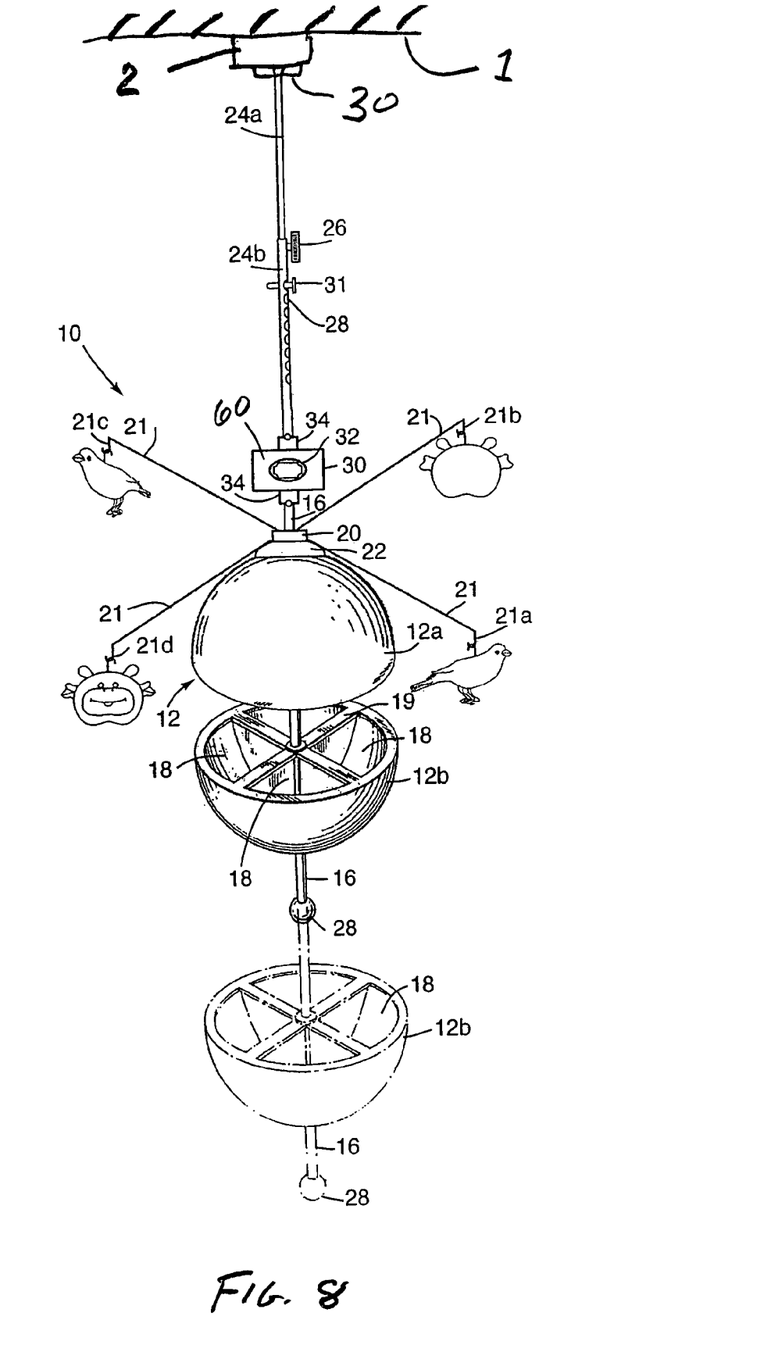
FIG. 8 is a perspective view of the preferred embodiment of the present invention mounted to a ceiling and shown in extended and retracted positions.
Figure 9:
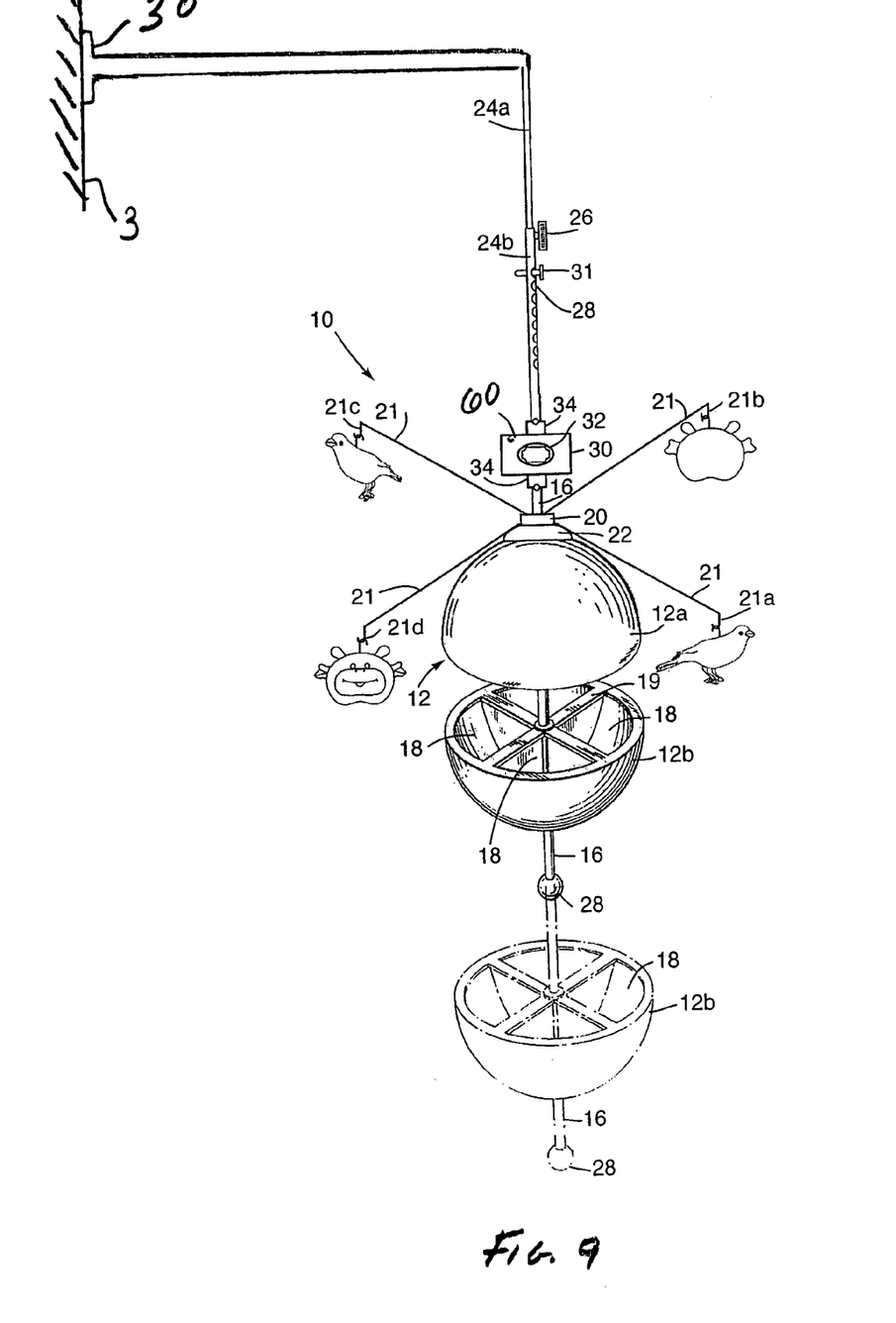
FIG. 9 is a perspective view of the preferred embodiment of the present invention mounted to a wall and shown in extended and retracted positions.
Figure 10:
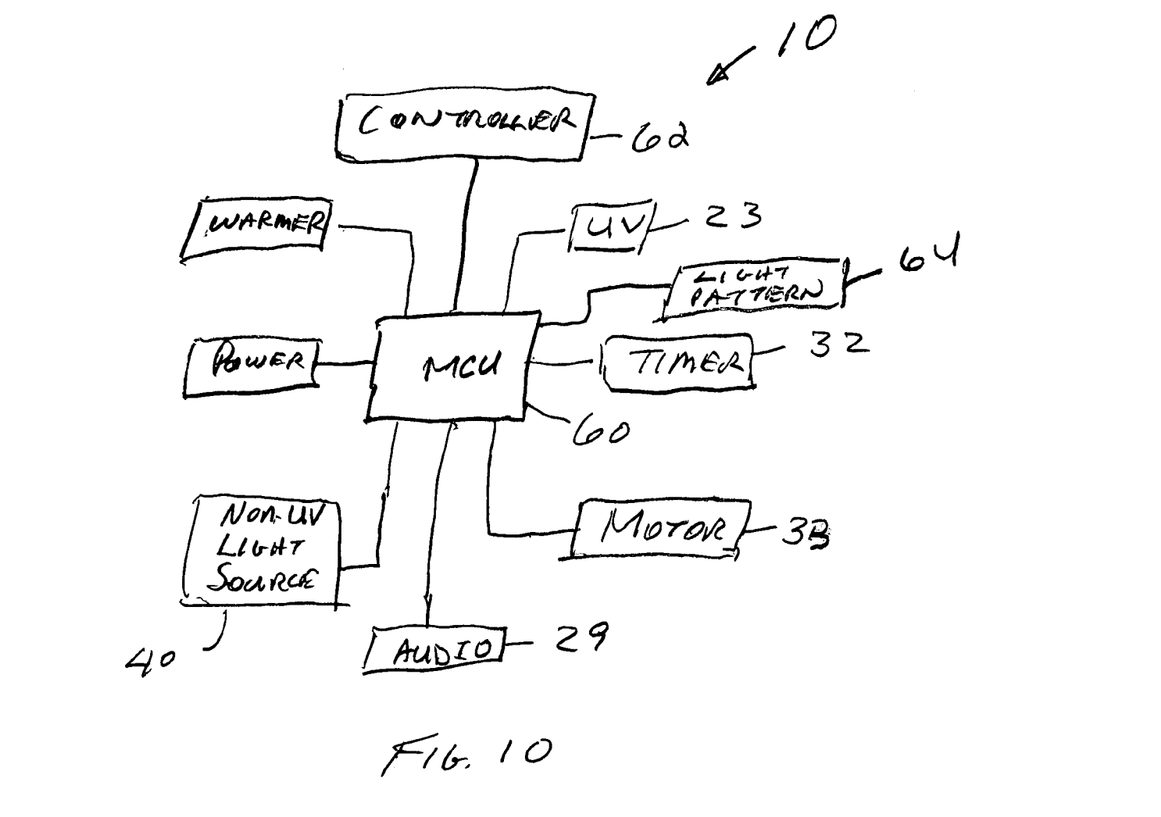
FIG. 10 is an electrical block diagram of the preferred embodiment of the present invention incorporating microcontroller.

With reference to the drawings, FIGS. 1 to 10 depict the preferred embodiment of the instant invention which is generally referenced as an infant cognitive stimulating sterilizing device and, or by numeric character 10. The instant invention is an improvement over the invention disclosed in U.S. Pat. No. 3,711,021, which is incorporated by reference herein, but does not necessarily share the same reference numerals, and has been adapted for an unrelated use. The instant invention 10 comprises a mobile-like device designed for supporting and providing at least one UV light source that attacks and deteriorates airborne organisms, such as bacteria, molds and viruses, releases an air freshener and provides visual and, or audible stimulation to an infant. Power may be received through an internal cord hard-wired to existing power or external cord 40 that plugs into an AC outlet, both of which run through the support rods 24, 16 to drive mechanism 30. Alternatively, the instant invention 10 may be powered by a DC power source, such as batteries. The drive mechanism 30 preferably includes a microprocessor 60 in electrical communication with the ultraviolet (UV) light source 23 for automatically energizing and de-energizing the UV light source 23 according to preset times through an internal or external timer 32. The instant invention 10 may comprise a housing 12 having a variety of geometric shapes, such as a sphere, cube, elliptical, animal or plant.

With reference to FIGS. 1-10, the cognitive stimulating sterilizing device 10 generally comprises a housing 12 having two halves 12a, 12b retractably joinable together along a support rod 16 for opening and closing the housing 12; retractable housing support rod 16 for supporting and facilitating the opening and closing of the housing 12; telescopic mounting rod 24 for supporting and adjusting the height of the housing 12; mounting bracket 30 for mounting the device 10 to a ceiling 1 or wall 3 or to a crib, changing table or similar furniture; mobile support rack 21 with hooks 21a-d for removably mounting infant related items 3 designed for facilitating visual stimulation in infants, at least one ultraviolet light source 23 for sterilizing items in the housing 12 and the surrounding area; drive system 30 having a microcontroller 60 with an internal or external timer 32 for automatically applying and removing power to and from the UV light source 23 at one or more preset times; at least one incandescent lamp or light bulb 40 for illuminating the interior of the housing 12 and, or surrounding area when the housing is open; and sound producing device 29 for audible stimulation. The instant invention 10 may also comprise visible entertaining color light source or sources 64, which may provide light patterns, using LED's or other light sources. The audio device 29 may comprise digital music sources such as an MP3 or I-Pod and USB interfacing. The audio source 29 and entertaining light source(s) 64 are preferably driven by the microcontroller 60, but may be controlled by a separate controller 62. The instant invention 10 may be powered by rechargeable batteries and, or batteries that it can recharge and use. The instant invention 10 may be electrically designed to operate with a wall transformer.

With reference to FIGS. 1-10, the lower housing half 12b comprises a plurality of compartments 18, 18a, 18b for holding items to be stored and sterilized. The shape and number of compartments may vary. The instant invention 10 may include an air freshener 39 that releases a fragrance when the housing 12 is opened. The upper housing half 12a supports and stores the UV light source 23, audio source 29 and light bulb 40 and may also store an air freshener 39, battery compartment 14 and light reflectors 27. The device 10 may include a motor 33 in the drive mechanism 30 for rotating the mobile support rack 21. The housing 12 preferably comprises lightweight molded plastic.

The UV source 23 comprises at least one UV light bulb 23, such as an ultraviolet germicidal 15-watt to 25-watt hot cathode UV lamp, preferably in the shape of a ring. In the preferred embodiment, power is applied to the ultraviolet light (UV) source 23 when the housing 12 is closed wherein the upper and lower halves 12a, 12b operate as switch or to trigger a switch. The UV light generated by the light source 23 sterilizes items in the housing 12 for a predetermined period of time, such as 2-6 minutes. The timer 32 removes power from the UV light source 23 after the predetermined time period. When the housing 12 is opened, ultraviolet light emanates from the housing 12 to sanitize the surrounding area. The housing 12 may include at least one reflector 27 for directing the UV light. The audio source 29 plays music, stories or other sounds that are comforting, entertaining and, or educational for the infant. The audio source 29 may have it's own switch and, or may be activated when the housing is opened or closed. The instant invention 10 preferably includes a timer 32 that removes power from the UV light source 23 after a preset time as adjusted by the operator. The timer 32 may be supported in the drive mechanism 30 and, or in electrical communication with the motor 33 that rotates the mobile 21 for removing power from the motor 33. The timer 32 may be electrically connected to the audio source 29 for removing power from it after a predetermined period of time. A full time cycle could be two minutes to six minutes, or some other selected time. Objects are placed in or near the housing 12 for receiving a direct, concentrated source of sterilizing UV from the UV light source 23.

The cognitive stimulating sterilizing device 10 preferably includes a mobile support rack 21 having hooks 21a-d to interchangeably support animated objects adapted for enjoyment by infants. The number of arms and hooks may vary without departing from the scope and spirit of the instant invention. The mobile support rack 21 may be static but preferably rotates. The motor 33 in the drive system 30 rotates the mobile 21. The instant invention 10 may include a ring 22 rotatably engaged with the upper housing half 12a and electrically connected to the drive system 30 for supporting and rotating the mobile support rack 21, which projects outward therefrom. Alternatively, the mobile support rack 21 may be connected to the upper or lower housing 12a, 12b. The drive system 30 comprises a motor 33 for turning the ring 22, upper housing 12a and, or lower housing 12b thereby causing the mobile support rack 21 to rotate. The timer 32 may also be used for removing power from the motor after a predetermined period of time. In an alternative embodiment, the invention 10 may include a control circuit for controlling when power is supplied to the motor and, or ultraviolet light source 23.

With reference to FIGS. 1-5 and 7-10, the upper housing half 12a comprises a bowl shape defining an interior volume 13, at least one compartment 18 and support rod aperture 17. The upper housing half 12a may include compartments 18, 18a, 18b having different shapes and sizes. The upper housing 12a supports at least one UV light source 23 and may also support reflectors 27, audio source 29 and air fresheners 39. The upper housing 12a may also include a battery compartment 14 for DC powered versions. A transparent panel 11 may be defined by or incorporated in the upper housing 12a for releasing light from the incandescent lamp 40. Power may be provided to the lamp 40 when the housing 12 is opened or closed or by way of a separate switch. In another embodiment, the transparent panel 11 may be closed to block the passage of light. The support rod 16 passes through the aperture 17 in the upper housing 12. The upper housing 12a is secured to the support rod 16. A slip coupling 20 may mechanically connect the ring 22 to the motor for rotating the ring 22 without rotating the housing 12. Alternatively, the ring 22 may be connected to the upper housing 12a and the coupling 20 to the support rod 16 for rotating the entire assembly.

With reference to FIGS. 1-5 and 7-10, the lower housing 12b preferably comprises a plurality of compartments 18, 18a and, or 18b defined by partitions 19 within its volume for supporting and holding items that need to be sterilized and accessible, such as powder, lotion and, or other infant hygiene items. The lower housing 12b may include a warming device 38, which may be cylindrical or shaped like the compartment 18, for warming bottles 2 and, or wipes. The warmer may be built into the compartment 18 and preferably comprises a heater device as is known in the art. The warmer is electrically connected to the source for receiving power and may comprise a separate switch. The instant invention 10 may comprise removable cups 36 adapted for insertion in the compartments. The removable cups 36 comprise a pair of side walls intersecting at right angles and a third shell-shaped side wall extending from the other ends of sidewalls. The sidewalls terminate at their upper edges in an outwardly extending peripheral flange and are suitably sized so that when the cup 36 is placed in the corresponding conforming compartment 18 the bottom surfaces of the flange sits on the compartment rim. A removable cup 36 enables the user to easily remove the cup for placement on a table or other location where needed.

The housing halves 12a, 12b are secured to the support rod 16. The support rod 16 preferably comprises telescopic tubes that facilitate the opening and closing of the housing 12. The positioning of the lower housing 12b relative to the upper housing 12 is maintained by locking the rod support's 16 tube in a selected position. The support rod 16 may be locked by a twist lock, tabs, spring-loaded buttons for engaging detents or holes or pins for placement in apertures. Alternatively, the rod support 16 may be extended and retracted by a retraction unit 26, such as that described in U.S. Pat. No. 3,711,021. In an alternative embodiment, the lower housing half 12b may slide up and down the rod 16 and interlock with the upper housing half 12a to close the housing 12.

The mounting rod 24 extends from the support rod 16 in a unibody construction or is otherwise mechanically joined to the support rod 16 by the drive system 30 or a known coupling. The mounting rod 24 comprises an adjustable, inverted L-shaped or hook-shaped tube system having a clamp 30 that facilitates attachment to a crib or changing table so the housing attachment end is suspended over the child. The mounting rod 24 comprises an upper mounting rod 24a telescopically joined to a lower mounting rod 24b for slidably adjusting the height of the housing 12. The height of the upper mounting rod 24a may be maintained by retaining screw system 26, spring loaded buttons on one rod with detents or apertures on the other rod, or pin 31 for inserting through apertures on the rods 24a, b when aligned. The clamp 30 preferably comprises a spring-loaded clamp 30 that grips furniture when released. Power wires 41 are fed through the mounting rod 24 and support rod 16 for supplying power to the motor 33, timer 32, UV light source 23 and audible source 29

The drive system 30 comprises the control components of the instant invention 10 and is mounted to the support rod 16 and upper mounting rod 24a. The drive system 30 comprises a motor 33 for rotating the ring 22 and, or support rod 16 and, or timer 32 for removing power from the motor 33, UV light source 23, retraction unit 26 and, or audio source 29. Additional knobs and, or switches may be provided on the drive system 30 for individual control of these components 33, 23, 26, 29.

The instant invention has been shown and described herein in what is considered to be the most practical and preferred embodiment. It is recognized, however, that departures may be made therefrom within the scope of the invention and that obvious structural and/or functional modifications will occur to a person skilled in the art.

What is claimed is:

1. A cognitive stimulating and sterilizing system for holding items and mentally stimulating infants while sanitizing the surrounding area and selected objects, the system comprising:
    a housing having an upper receptacle and lower receptacle;
    a support rod for supporting said housing and facilitating the slidable movement of said upper and lower receptacles for opening and closing said housing, said rod comprising at least two rods telescopically joined together;
    mounting rod mechanically communicated with said support rod for adjusting and setting the height that said housing is suspended;
    means for supporting said system from a ceiling;
    power receiving means for providing and removing electrical power to and from said system, respectively; and
    an ultraviolet light source supported in said housing for generating and emanating ultraviolet light at a wavelength calculated to disinfect objects in the surrounding area and adapted for receiving power from said power receiving means.

2. A system as recited in claim 1, further comprising:
   microcontroller means, in electrical communication with said ultraviolet light source, for automatically activating and de-activating said ultraviolet light source according to pre-defined settings.

3. A system as recited in claim 1, further comprising:
   means, in electrical communication with said power receiving means, for providing lights of various colors and patterns.

4. A system as recited in claim 1, further comprising:
   a controller, in electrical communication with said microcontroller, for facilitating user control.

5. A system as recited in claim 1, further comprising:
   audio means, in electrical communication with said microcontroller, for playing prerecorded audio.

6. A system as recited in claim 1, further comprising:
   means for recharging batteries.

7. A cognitive stimulating and sterilizing system for holding items and mentally stimulating infants while sanitizing the surrounding area and selected objects, the system comprising:
    a housing having an upper receptacle and lower receptacle;
    a support rod for supporting said housing and facilitating the slidable movement of said upper and lower receptacles for opening and closing said housing, said rod comprising at least two rods telescopically joined together;
    mounting rod mechanically communicated with said support rod for adjusting and setting the height that said housing is suspended;
    means for supporting said system from a wall;
    power receiving means for providing and removing electrical power to and from said system, respectively; and
    an ultraviolet light source supported in said housing for generating and emanating ultraviolet light at a wavelength calculated to disinfect objects in the surrounding area and adapted for receiving power from said power receiving means.

8. A system as recited in claim 7, further comprising:
   microcontroller means, in electrical communication with said ultraviolet light source, for automatically activating and de-activating said ultraviolet light source according to pre-defined settings.

9. A system as recited in claim 7, further comprising:
   means, in electrical communication with said power receiving means, for providing lights of various colors and patterns.

10. A system as recited in claim 7, further comprising:
    a controller, in electrical communication with said microcontroller, for facilitating user control.

11. A system as recited in claim 7, further comprising:
    audio means, in electrical communication with said microcontroller, for playing prerecorded audio.

12. A system as recited in claim 7, further comprising:
    means for recharging batteries.

13. A cognitive stimulating and sterilizing system for holding items and mentally stimulating infants while sanitizing the surrounding area and selected objects, the system comprising:
    a housing having an upper receptacle and lower receptacle;
    a support rod for supporting said housing and facilitating the slidable movement of said upper and lower receptacles for opening and closing said housing, said rod comprising at least two rods telescopically joined together;

mounting rod mechanically communicated with said support rod for adjusting and setting the height that said housing is suspended;

microcontroller means, in electrical communication with said ultraviolet light source, for automatically activating and de-activating said ultraviolet light source according to pre-defined settings;

means for mounting said system;

power receiving means for providing and removing electrical power to and from said system, respectively; and an ultraviolet light source supported in said housing for generating and emanating ultraviolet light at a wavelength calculated to disinfect objects in the surrounding area and adapted for receiving power from said power receiving means.

14. A system as recited in claim 13, further comprising:
means, in electrical communication with said power receiving means, for providing lights of various colors and patterns.

15. A system as recited in claim 13, further comprising:
a controller, in electrical communication with said microcontroller, for facilitating user control.

16. A system as recited in claim 13, further comprising:
audio means, in electrical communication with said microcontroller, for playing prerecorded audio.

17. A system as recited in claim 13, further comprising:
means for recharging batteries.

* * * * *